(12) United States Patent
Kawada et al.

(10) Patent No.: US 9,297,649 B2
(45) Date of Patent: Mar. 29, 2016

(54) PATTERN DIMENSION MEASUREMENT METHOD AND CHARGED PARTICLE BEAM APPARATUS

(75) Inventors: Hiroki Kawada, Tokyo (JP); Norio Hasegawa, Tokyo (JP); Toru Ikegami, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 257 days.

(21) Appl. No.: 14/001,433

(22) PCT Filed: Dec. 12, 2011

(86) PCT No.: PCT/JP2011/006907
§ 371 (c)(1),
(2), (4) Date: Oct. 22, 2013

(87) PCT Pub. No.: WO2012/114411
PCT Pub. Date: Aug. 30, 2012

(65) Prior Publication Data
US 2014/0048706 A1 Feb. 20, 2014

(30) Foreign Application Priority Data
Feb. 24, 2011 (JP) .................................. 2011-037771

(51) Int. Cl.
*G01B 15/06* (2006.01)
*G01N 23/225* (2006.01)
(Continued)

(52) U.S. Cl.
CPC ................ *G01B 15/06* (2013.01); *G01N 23/00* (2013.01); *H01J 37/222* (2013.01); *H01J 37/28* (2013.01);
(Continued)

(58) Field of Classification Search
CPC ... G01B 15/06; G01N 23/22; G01N 23/2202; G01N 23/2251; H01J 37/222; H01J 37/28; H01J 2237/24578; H01J 2237/2816; H01J 2237/2817
See application file for complete search history.

(56) References Cited

U.S. PATENT DOCUMENTS 7,285,777 B2 * 10/2007 Kawada ................ G01B 15/00
250/307
7,659,508 B2 2/2010 Nasu et al.
(Continued)

FOREIGN PATENT DOCUMENTS

JP 2007-003535 A 1/2007
JP 2007-285906 A 11/2007
(Continued)

OTHER PUBLICATIONS

English translation of International Search Report issued in International Patent Application No. PCT/JP2011/006907 dated Mar. 13, 2012.

*Primary Examiner* — Jack Berman
(74) *Attorney, Agent, or Firm* — McDermott Will & Emery LLP

(57) ABSTRACT

The present invention aims to provide a pattern dimension measurement method for accurately measuring an amount of shrinkage of a pattern that shrinks and an original dimension value before the shrinkage and a charged particle beam apparatus.

In order to attain the above-mentioned object, there are proposed a pattern dimension measurement method and a charged particle beam apparatus that are characterized by: forming a thin film on a sample including the pattern after carrying out beam scanning onto a first portion of the pattern; acquiring a first measurement value by scanning a beam onto a region corresponding to the first portion on which the thin film is formed; acquiring a second measurement value by scanning a beam onto a second portion that has identical dimensions as those of the first portion on design data; and finding the amount of shrinkage of the pattern based on subtraction processing of subtracting the first measurement value from the second measurement value.

7 Claims, 13 Drawing Sheets

(51) Int. Cl.
*H01J 37/28* (2006.01)
*H01J 37/22* (2006.01)
*G01N 23/00* (2006.01)
*H01J 37/244* (2006.01)

(52) U.S. Cl.
CPC ...... *H01J 37/244* (2013.01); *H01J 2237/24578* (2013.01); *H01J 2237/2816* (2013.01); *H01J 2237/2817* (2013.01)

(56) References Cited

U.S. PATENT DOCUMENTS

| | | | |
|---|---|---|---|
| 7,720,632 B2 * | 5/2010 | Kurihara | H01L 22/12 250/310 |
| 7,910,886 B2 * | 3/2011 | Kawada | B82Y 15/00 250/310 |
| 9,110,384 B2 * | 8/2015 | Omori | G03F 7/70625 |
| 2005/0247876 A1 | 11/2005 | Kawada et al. | |
| 2012/0037801 A1 | 2/2012 | Mochizuki et al. | |
| 2014/0246585 A1 * | 9/2014 | Ohashi | G01B 15/04 250/310 |

FOREIGN PATENT DOCUMENTS

| | | |
|---|---|---|
| JP | 2008-232818 A | 10/2008 |
| JP | 2012-002765 A | 1/2012 |
| WO | 03/021186 A1 | 3/2003 |
| WO | 03/098149 A1 | 11/2003 |
| WO | 2010/119641 A1 | 10/2010 |

\* cited by examiner (a)

(b)

(c)

(d)

| ID | EP | Resist | ALD | | Shrink | Result |
|---|---|---|---|---|---|---|
| | | CD1 | CD1 | CD2 | | |
| | | | | | | |
| | | | | | | |
| | | | | | | |
| | | | | | | |
| | | | | | | |
| | | | | | | |
| | | | | | | |

| Pattern | SEM condition | | | offset value | approximate function |
|---|---|---|---|---|---|
| | Beam current | frame | scan speed | | |
| A | | | | | |
| | | | | | |
| | | | | | |
| | | | | | |
| B | | | | | |
| | | | | | |
| | | | | | |
| | | | | | |
| C | | | | | |
| | | | | | |
| | | | | | |

PATTERN DIMENSION MEASUREMENT METHOD AND CHARGED PARTICLE BEAM APPARATUS

RELATED APPLICATIONS

This application is the U.S. National Phase under 35 U.S.C. §371 of International Application No. PCT/JP2011/006907, filed on Dec. 12, 2011 which in turn claims the benefit of Japanese Application No. 2011-037771, filed on Feb. 24, 2011, the disclosures of which Applications are incorporated by reference herein.

TECHNICAL FIELD

The present invention relates to a pattern dimension measurement method and a charged particle beam apparatus, and more specifically to a pattern dimension measurement method for measuring a pattern having a possibility that its volume decreases by beam irradiation and a charged particle beam apparatus.

BACKGROUND ART

In manufacturing and inspection processes of functional device products, such as a semiconductor device and a thin film magnetic head, that are manufactured by micro processing of their surfaces, the scanning electron microscope is widely used for measurement (hereinafter called "length measurement") and appearance inspection of a pattern that is processed. The scanning electron microscope is an apparatus for performing the measurement by scanning a beam having an arrival energy of a few hundreds electron volts on a pattern that is a measurement object. However, for example, a photoresist (ArF resist) responsive to an argon fluoride excimer laser beam decreases (shrinks) in volume by irradiation of an electron beam although it is suitable for formation of a minute circuit pattern. Therefore, it is difficult for the scanning electron microscope to measure exact dimensions before the volume decrease.

Against such a problem, the patent literatures 1, 2 propose a technique of estimating a dimension value before the volume decrease by plotting a relationship between measurement times and the amount of volume decrease and fitting a curve representing the relationship with an approximate function. That is, estimating the dimensions before volume decrease using extrapolation is proposed.

On the other hand, responding to a request of further minute fabrication of the semiconductor device, a pattern formation method called self-aligned double patterning (SADP) has become adopted. The SADP is a technology of creating patterns arranged with a very narrow pitch equal to or less than an exposure limit that the conventional aligner can reach. Subjecting the pattern formed by such a pattern formation method to a measurement object of the SEM is disclosed, for example, in Patent Literature 3.

CITATION LIST

Patent Literature

Patent Literature 1: WO2003/021186 (corresponding to U.S. Pat. No. 7,659,508)
Patent Literature 2: WO2003/098149 (corresponding to U.S. Pat. No. 7,285,777)
Patent Literature 3: WO2010/119641

SUMMARY OF INVENTION

Technical Problem

Recently, miniaturization of the semiconductor devices has proceeded further and a phenomenon that its pattern tends to shrink by beam irradiation has been recognized more notably. Shrinkage occurs greatly after the beam irradiation starts, and its degree tends to converge gradually according to lapse of time. Especially, shrinkage in an early stage of the beam irradiation is large, and it is becoming difficult to perform fitting with an approximate function with high accuracy, as is disclosed in Patent Literatures 1, 2. Moreover, since a value found by extrapolation is an estimate to the last, if the processing proceeds to a more minute level, there will also be a possibility that measurement accuracy cannot be secured. The patent literature 3 does not refer to anything at all about measuring the pattern that shrinks.

Hereinafter, there are proposed a pattern dimension measurement method that aims at measuring an amount of shrinkage of a pattern that shrinks or an original dimension before the shrinkage in a semiconductor process including a thin film formation process such as of the SADP, and a charge particle beam apparatus for realizing the measurement.

Solution to Problem

As one mode for attaining the above-mentioned object, in the pattern dimension measurement method for measuring dimensions of the pattern based on a detection signal obtained by scanning a beam onto a pattern formed on a sample, there is proposed a pattern dimension measurement method characterized by: forming a thin film to a sample including the pattern after carrying out beam scanning onto a first portion of the pattern; acquiring a first measurement value of the pattern on which the thin film is formed by scanning a beam onto a region corresponding to the first portion on which the thin film is formed; acquiring a second measurement value of the pattern on which the thin film is formed by scanning the beam onto a second portion having identical dimensions as those of the first portion on design data; and finding the amount of shrinkage of the pattern based on subtraction processing of subtracting the first measurement value from the second measurement value.

Moreover, there is proposed a pattern dimension measurement method for measuring the original dimension before the shrinkage based on addition of the above-mentioned amount of shrinkage and a third measurement value obtained based on beam scanning onto the first portion before the thin film formation.

Furthermore, as another mode for attaining the above-mentioned object, in a charged particle beam apparatus that has a charged particle source for emitting a charged particle beam, a scanning position control unit for varying a scanning position of the charged particle beam emitted from the charged particle source, and a dimension measurement apparatus for measuring the dimensions of the pattern within the scanning positions based on the detection signal obtained by the beam scanning to the scanning position of the charged particle beam, there is proposed a charged particle beam apparatus characterized in that the scanning position control unit sets the scanning position in a first portion on the sample and in a second portion having identical dimensions as those of a pattern located in the first portion on the design data, and the dimension measurement apparatus outputs a dimension value based on the detection signal obtained in the first portion and the second portion.

Advantageous Effect of Invention

According to the above-mentioned one mode, it becomes possible to measure the pattern that shrinks by irradiation of a beam with high accuracy.

DESCRIPTION OF EMBODIMENTS

An embodiment that will be explained below relates to an apparatus for measuring dimensions of a pattern formed on a sample based on an image obtained by a microscope or a detection signal, a computer program for making a computer execute the measurement, or a storage medium that can be read by the computer for storing the program. The embodiment relates especially to a scanning electron microscope that scans a minute pattern and measures its dimension, and relates to a scanning electron microscope (an SEM) capable of suppressing the shrinkage occurring in the sample by electron beam irradiation and an error of the measurement value by electrification and making an image clearer by increasing the amount of detection of the secondary electrons.

Resists that have started to be used recently responding to a requirement of formation of minute patterns, such as ArF resist, have a possibility that a resist pattern will shrink depending on an irradiation condition of an electron beam. Since in the shrunk pattern, its width has become small as compared with a dimension value of the pattern before the shrinkage, even if the pattern after the shrinkage is measured, a correct measurement value cannot be obtained.

So, in this embodiment, an apparatus for deriving the shrinkage based on an actual measurement value and others will be explained. According to a measurement method explained below, since a reduction dimension of a line width by the shrinkage can be found based on the actual measurement value, a measurement having accuracy necessary to evaluate the minute process that requires a precision of sub-nanometer becomes possible. On the other hand, when an amount of shrinkage is found based on multiple times of measurements, there is a tendency that the amount of shrinkage based on a first measurement becomes large compared with the amount of shrinkage of the second times and later times. Therefore, when finding the amount of shrinkage by extrapolation, measurement accuracy may not be sufficient.

In this embodiment, since the amount of shrinkage can be found based on the actual measurement value as described above, not finding the amount of shrinkage and dimensions of the pattern by the extrapolation, sufficient measurement accuracy is securable.

Below, an apparatus for measuring a pattern that shrinks with high accuracy etc. will be explained in detail using drawings.

Figure 3:
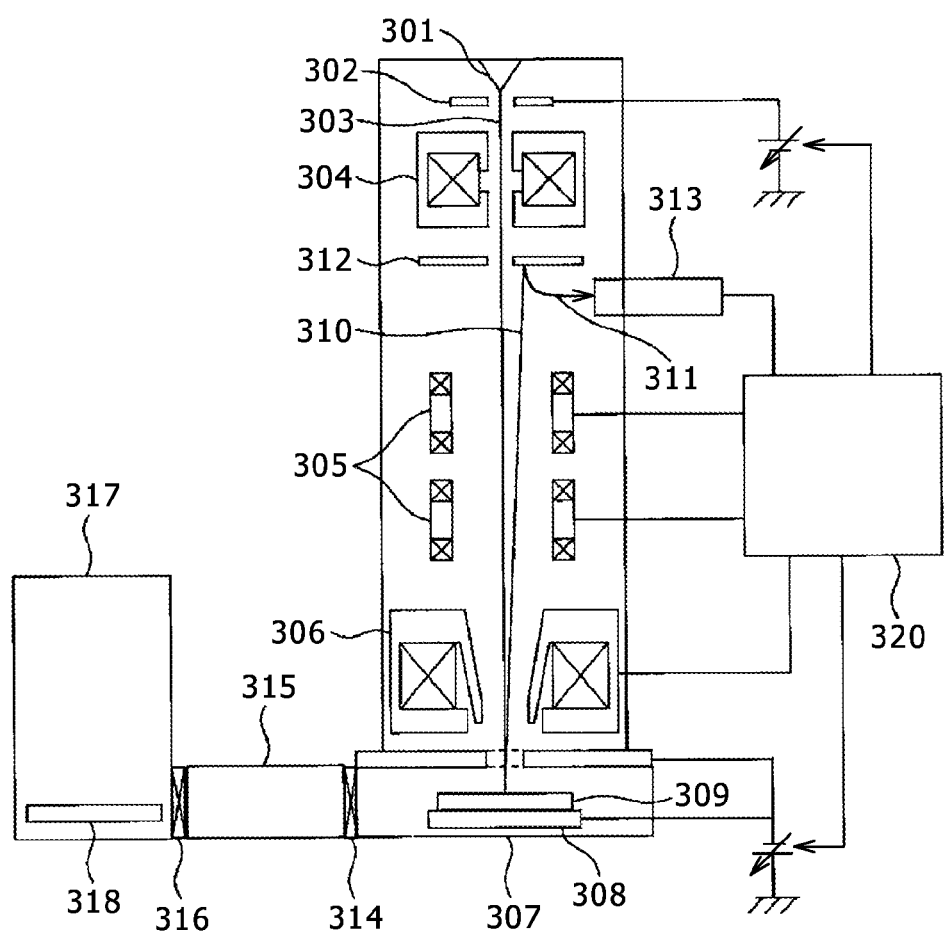
FIG. 3 is a diagram showing an outline of a scanning electron microscope.

FIG. 3 is a diagram showing an outline of the SEM that is one mode of the measuring apparatus. Incidentally, although this embodiment explains an example in which the SEM is applied as the measuring apparatus, it is also possible to apply the following embodiment to other apparatuses (for example, focused ion beam (FIB) apparatus) as long as they have a common problem that a pattern shrinks by the beam irradiation.

An electron beam 303 that is extracted from an electron source 301 by an extraction electrode 302 and is accelerated by an unillustrated accelerating electrode is focused by a condenser lens 304 that is one mode of a focusing lens, and subsequently is scanned onto a sample 309 one-dimensionally or two-dimensionally by a scanning deflector 305. The electron beam 303 is reduced in speed by a negative voltage applied to an electrode built in a sample stage 308, and at the same time, is focused by a lens effect of an objective lens 306 to be irradiated on the sample 309.

When the sample 309 is irradiated with the electron beam 303, electrons 310, such as the secondary electrons and the backscattered electrons, are emitted from the irradiation point. By an acceleration action based on the negative voltage applied to the sample, the emitted electrons 310 are accelerated in an electron source direction, and are collided with a conversion electrode 312 to produce secondary electrons 311. The secondary electrons 311 emitted from the conversion electrode 312 are captured by a detector 313, and an output of the detector 313 varies depending on the amount of captured secondary electrons. Brightness of an unillustrated display varies in response to this output. For example, in the case of forming a two-dimensional image, an image of a scan region is formed by synchronizing a deflection signal to the scanning deflector 305 and the output of the detector 313. Moreover, in the scanning electron microscope illustrated in FIG. 3, a deflector (not illustrated) for moving the scan region of the electron beam is provided. This deflector is used in order to form an image of the pattern of an identical shape that exists in a different position and others. This deflector is also called an image shift deflector, which makes it possible to move a position of field of view (FOV) of the electron microscope without performing sample movement by the sample stage, etc. It may be good to configure so that the image shift deflector and the scanning deflector may be specified to be a common deflector, and a signal for image shifting and a signal for scanning may be superimposed and supplied to the deflector.

Incidentally, although the example of FIG. 3 explains the example in which the electrons emitted from the sample are detected after temporarily converting them with the conversion electrode, naturally the configuration is not limited to such one, and it is possible to adopt a configuration, for example, where a detection surface of an electron multiplier or a detector is disposed on a trajectory of accelerated electrons.

A control unit 320 controls each configuration of the scanning electron microscope and, at the same time, has a function of forming an image based on the detected electrons and a function of measuring a pattern width of a pattern formed on the sample based on an intensity distribution of the detected electrons called a line profile.

A sample 318 is carried into a load-lock chamber 315 through a mini-environment 317, and subsequently is conveyed into a sample chamber 307. Gate valves 314, 316 are provided in the load-lock chamber 315, which is configured so that evacuation in the load-lock chamber 315 can be done.

Figures 4, 5:
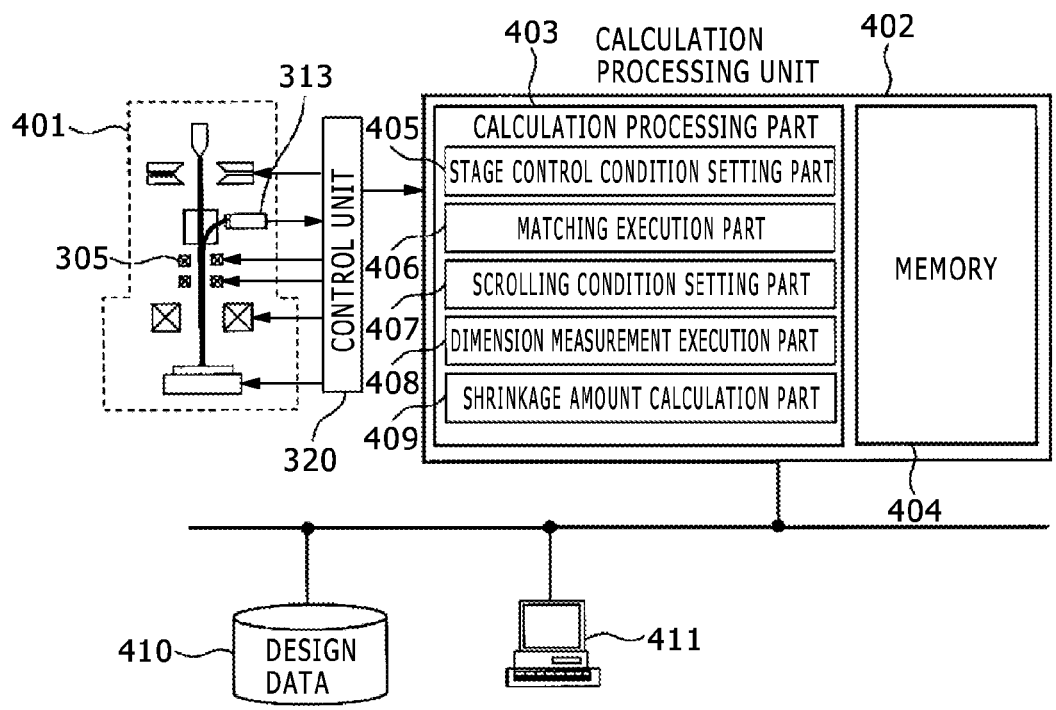
FIG. 4 is a diagram showing an outline of a semiconductor device measurement system including the scanning electron microscope.
FIG. 5 is a diagram showing a display example of the measurement results that are put in a database.

FIG. 4 is a detailed explanatory diagram of a measurement or inspection system including the SEM. This system includes an SEM body 401, a control unit 320 of the SEM body, and an arithmetic processing unit 402. The arithmetic processing unit 402 incorporates an arithmetic processing part 403 for supplying a predetermined control signal to the control unit 320 and memory 404 for storing obtained image information and recipe information.

The electrons emitted from the sample are captured by the detector 313, and are converted into a digital signal by an A/D converter built in the control unit 320. Image processing according to the object is performed by image processing hardware, such as a CPU, an ASIC, and an FPGA built in the arithmetic processing unit 402. An arithmetic processing part 408 incorporates a stage control condition setting part 405 for setting movement conditions of the sample stage on which the sample is placed and a matching execution part 406 for executing template matching based on the obtained image. The template matching is a technique of pinpointing a point at which a taken image to be subjected to alignment and the template coincide based on coincidence degree determination using a normalized correlation method etc., and the matching execution part 406 specifies a desired position of the taken image based on the coincidence degree determination.

Moreover, the arithmetic processing part 403 incorporates a scrolling condition setting part 407 for setting a deflection condition of the deflector for image shift, a dimension measurement execution part 408 for measuring pattern dimensions based on the obtained detection signal (for example, the line profile), and a shrinkage amount calculation part 409 for measuring the amount of shrinkage and the pattern dimensions after the shrinkage based on the measurement value obtained by the dimension measurement execution part 408. In the dimension measurement execution part 408, the line profile is formed, for example, based on the detection signal and dimension measurement between peaks of the profile is performed. Details of the arithmetic processing part 403 will be described later. The stage control condition setting part 405 and the scrolling condition setting part 407 are both for deciding a beam scanning position, and the control unit 320 performs control of the scanning position based on setting information that is set by these setting parts.

Furthermore, the arithmetic processing unit 402 is connected with an input device 1411 having input means. A GUI (Graphical User Interface) for displaying an image, an inspection result, etc. for an operator etc. is displayed on a display provided in the input device 411.

Incidentally, it is also possible to assign a part or all of the control and processing in a calculation processing unit 1407 to the computer that mounts a CPU and memory capable of accumulating images and others, and to process and control them. Moreover, the input device 411 also functions as an imaging recipe creation device for creating an imaging recipe that includes coordinates of an electronic device necessary for inspection etc., a template for pattern matching used for positioning, photographing conditions, etc. manually or by utilizing design data stored in a design data storage medium 411 of the electronic device.

The input device 411 has a template creation part for cutting a part of a diagrammatic drawing image formed based on the design data and making it as a template, and the created template is registered in the memory 404 as a template of the template matching in the matching processing part 406 built in an image processing part 507.

The design data stored in the design data storage medium 410 is represented in a GDS format, an OASIS format, etc., and is stored in a predetermined form. Moreover, any design data can be used regardless of its kind as long as software for displaying the design data can display its format form and can treat it as graphic data. Moreover, the graphic data may be diagrammatic image information to which deformation processing is performed so that it may become close to a real pattern by performing exposure simulation instead of diagrammatic image information indicating an ideal shape of the pattern formed based on the design data.

Incidentally, although in the embodiment explained below, an example in which calculation of the amount of shrinkage, the pattern dimensions, etc. is executed in the arithmetic processing unit 402 will be explained, the embodiment is not limited to this and the embodiment may be configured to make a computer program perform later-described processing using a general-purpose calculation device for executing measurement processing.

Below, one mode of calculation of the amount of shrinkage executed by the arithmetic processing unit 402 will be explained.

Figure 1:
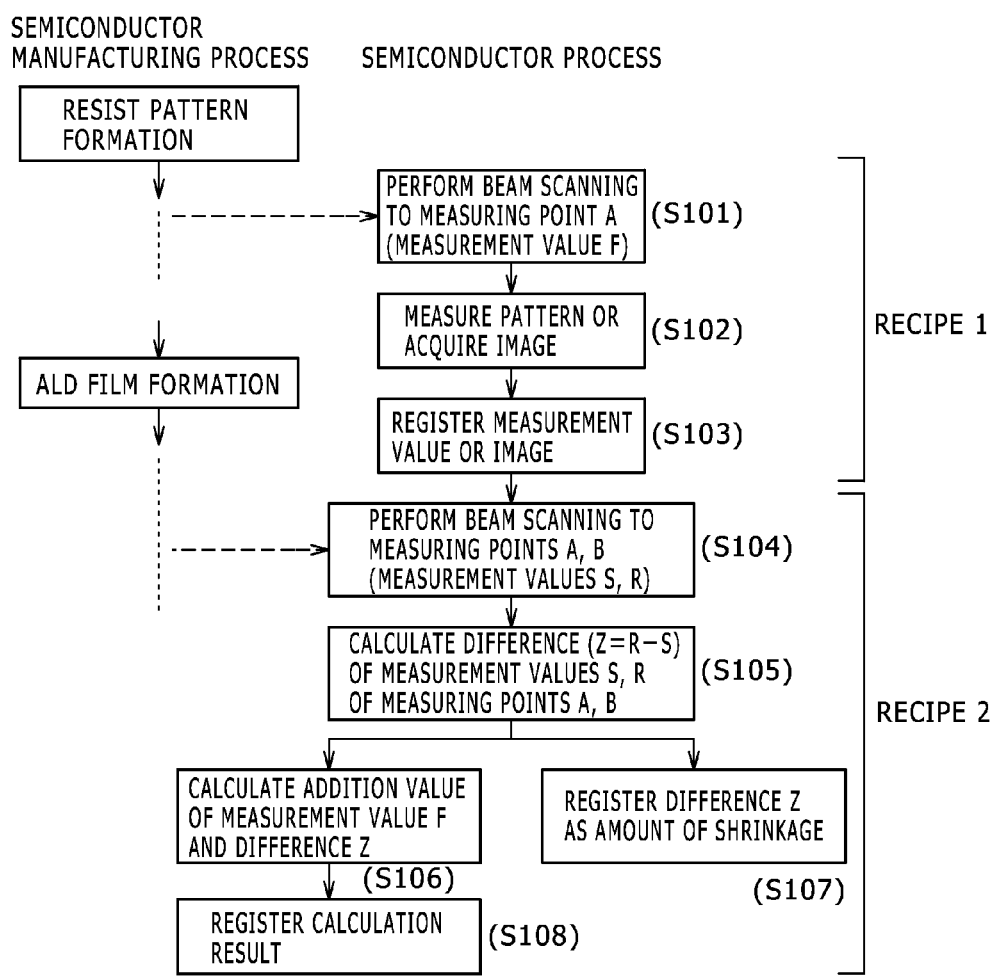
FIG. 1 is a flowchart showing a process of measuring an amount of shrinkage of a pattern that arises by beam irradiation.

FIG. 1 is a flowchart showing one example of a measuring process of the amount of shrinkage. Incidentally, although an example in which a pattern that is formed through a manufacturing process called SADP is measured will be explained, the present invention is not limited to this, but can be applied to general measurement of a pattern formed by a process in which a pattern that is to be measured shrinks and a film resistive to the beam irradiation is formed after the formation of the pattern that shrinks.

The SADP is a technology of creating patterns that are arranged with a very narrow pitch equal to or less than an exposure limit that the conventional aligner can reach. Specifically, a first mask layer is formed on the sample, the resist pattern is formed on the mask layer, and after being subjected to exposure processing and etching processing of the first mask layer, a second mask layer (for example, a film formed by an ALD (Atomic Layer Deposition) method) is formed. Then, after adjusting the etching condition so that apart of the second mask layer may remain, the second mask layer is etched, and etching processing is performed using a residual structure of the second mask layer as a mask, whereby pattern formation with a pitch equal to one half of the exposure limit is made possible.

Figure 2:
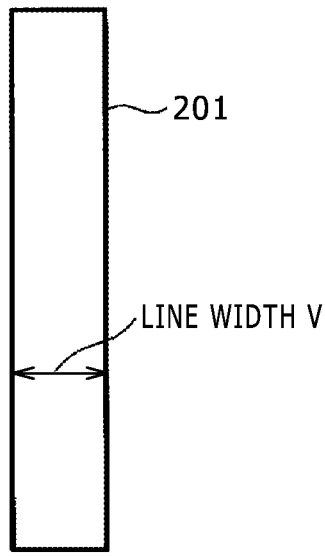
FIG. 2 is a diagram showing a relationship among a resist pattern, a pattern after thin film formation, and a beam scanning position.
Figure 2:
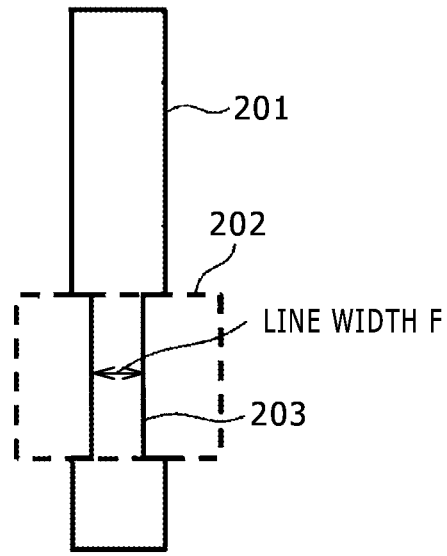
Figure 2:
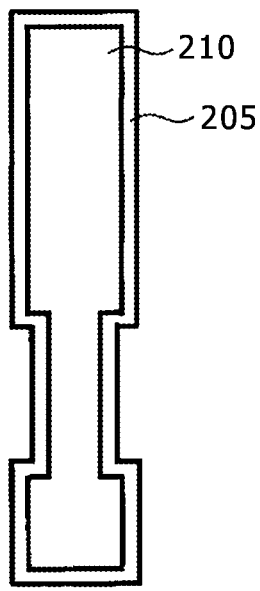
Figure 2:
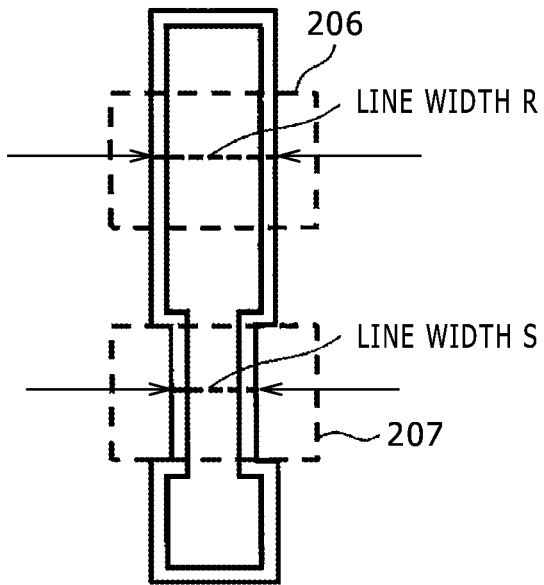

In the pattern formation process by the above SADP method, judgment as to whether the resist (a pattern that shrinks by the beam irradiation) etc. is properly formed is extremely important in evaluation of the semiconductor manufacturing process. The flowchart of FIG. 1 illustrates a measuring process that can properly evaluate the resist, especially. FIG. 2 is a diagram showing a relationship between manufacturing steps of the pattern and measuring points in the respective manufacturing processes.

Especially in this embodiment, a microscope or a dimension measurement apparatus will be explained that makes possible exact dimensions from which an influence of shrinkage that occurs in a core resist pattern is reduced by performing the length measurement after forming a hard mask for double patterning on the surface of the core resist pattern and outputting a length measurement value from which a thickness of the hard mask is subtracted as a line width measurement length value of the core resist pattern when measuring the line width of the core resist pattern of a pattern formed by the double patterning process.

FIG. 2(a) shows a resist pattern 201 formed through a resist formation process, and its pattern dimension (line width) is V. It is a main object in this embodiment to measure this line width V accurately. As illustrated in FIG. 2(b), when a scanning region is set at the measuring point A202 and beam scanning is performed (Step 101), the pattern shrinks. The measurement extracts a pattern dimension F at this time (a fourth measurement value) (Step 102). Incidentally, it may be good that an image including the pattern portion 203 that shrank is stored (Step 103) and the line width F is configured to be found when the amount of shrinkage is calculated later.

Next, as illustrated in FIG. 2(c), an ALD film 205 (for example, a SiN film of about 4 nm in thickness) that is one mode of a thin film is formed, subsequently, as illustrated in FIG. 2(d), scanning regions 206, 207 for measuring a line width R (a second measurement value) and a line width S (a first measurement value) are set, and beam scanning is performed (Step 104). Such control of scrolling is performed based on a movement quantity setup in the scrolling condition setting part 407. Here, the line width R becomes a dimension equal to a dimension of a pattern portion free from shrinkage added with a film thickness of the ALD film. On the other hand, the line width S becomes a dimension equal to a dimension of a shrink part added with the film thickness of the ALD film. That is, a difference between the line width R and the line width S (a third measurement value) can be defined as the amount of shrinkage.

Then, denoting this amount of shrinkage as Z, it becomes $$Z=R-S \quad \text{(Formula 1)}.$$

Since a place where the line width R is in the vicinity of the line width V and they are on the same line pattern, a difference of the line widths is so small that can be disregarded practically. It is possible to find the amount of shrinkage with high accuracy by designating a point having identical dimension as a reference point for calculating the amount of shrinkage. This difference is calculated at Step 105. Incidentally, an example in which only the difference is found is explained in this example, and if there exists another dimensional variation factor, it may be good that the amount of shrinkage and the pattern dimensions are configured to be found by four operations of the factor portion. Since the SiN film interrupts the electron beam at the time of measurement of the line widths S and R, the beam does not reach groundwork.

By adding the amount Z of shrinkage calculated as described above and the above-mentioned line width F (Formula 2), the dimension value V before the shrinkage is calculated (Step 106).

$$V=F+(R-S) \quad \text{(Formula 2)}$$

The line width F after the shrinkage added with the amount of zero shrinkage can be assumed as the line width V before the shrinkage. Alternatively, it may be good to register only the difference Z (Step 107), which is intended to be used for other calculations later. A concrete calculation method will be described later.

The line width V found as described above is registered as a dimension value before the shrinkage (Step 108). The dimension measurement and calculation as described above are performed by the dimension measurement execution part 408 and the shrinkage amount calculation part 409, and the measurement result is stored in the memory 404 or an external storage medium. Since it becomes difficult to measure the line width F accurately after the thin film was formed, it can be said that the above-mentioned technique is a very effective technique in measuring the amount of shrinkage or the line width before the shrinkage.

Incidentally, since Steps 101 to 103 and Steps 104 to 108 are measuring processes after mutually different manufacturing processes, respectively, operation programs (recipes) that store operating conditions of the SEM are prepared, respectively, and the measurement is performed using the each recipe. In this example, two kinds of recipes (a recipe 1 and a recipe 2) are stored in a storage medium in the control unit 320 or the memory 404 of the arithmetic processing unit 402 in advance, and either of them is used by switching as required. That is, it can be said that the SEM illustrated in FIG. 3 is an apparatus whose operation is controlled by at least two recipes.

FIG. 5 is a diagram showing a display example of the measurement results that are put in a database. ID (Identification) is an identification number assigned to the measuring point, and EP (Evaluation Point) is an identification number assigned to the measuring location. A value of the line width F is stored in CD1 of Resist, and values corresponding to the line width R and the line width S are stored in CD1 and CD2 of ALD, respectively. Thus, it becomes possible to easily realize a calculation of the amounts of shrinkage (R to S) and the line width V before the shrinkage (Result) by registering collectively the measurement results measured in different manufacturing processes in this way.

Incidentally, it may be good to store these measurement results in table calculation software of general purpose and make the software perform the above-mentioned calculation. In this case, what is necessary is just to enable the measuring apparatus to output the measurement results of the line widths F, R, and S.

Figure 6:
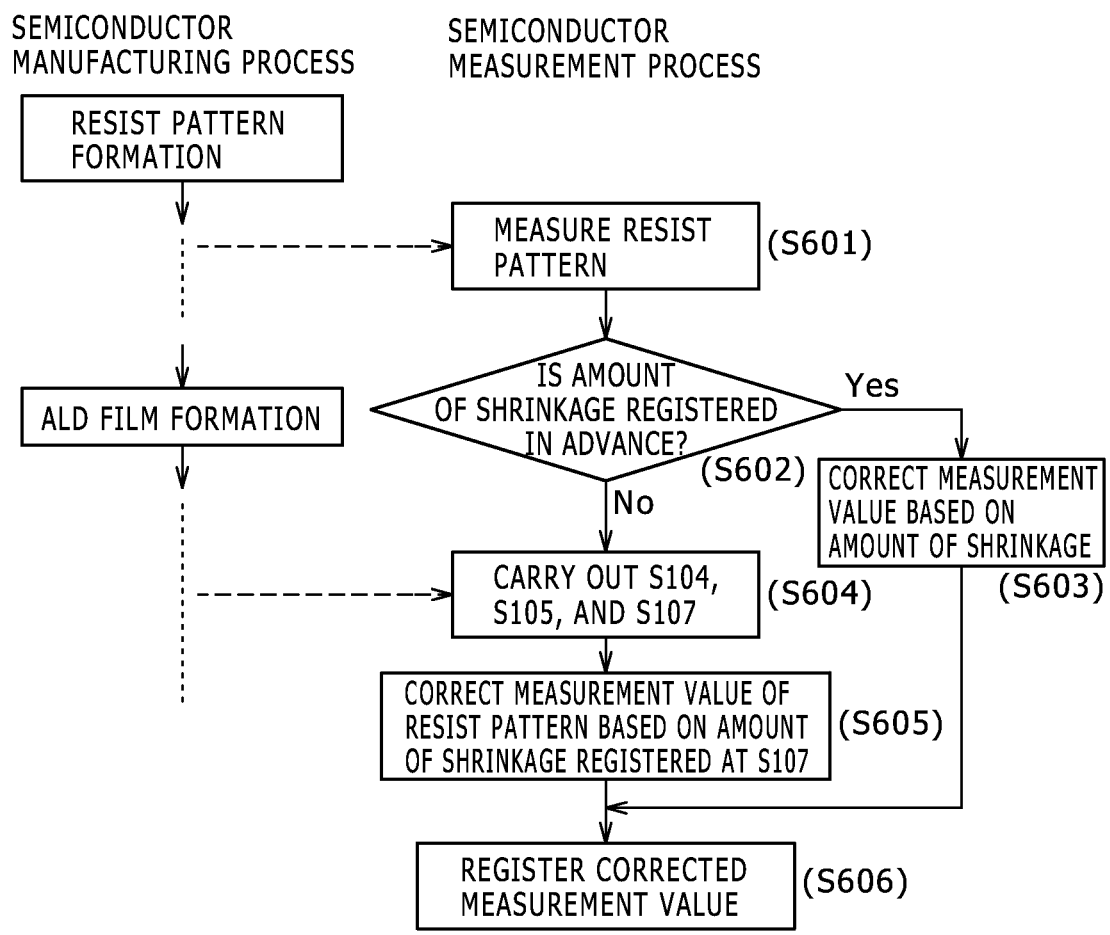
FIG. 6 is a flowchart showing a process of deriving a corrected measurement value with the amount of shrinkage of the pattern generated by the beam irradiation being corrected.

FIG. 6 is a flowchart showing a process of registering the amount of shrinkage in advance and calculating the measurement value before the shrinkage based on the registered amount of shrinkage. As explained previously, the amount of shrinkage varies according to the kind of a pattern (a combination of a material, pattern dimensions, a shape, etc.) and an optical condition of the SEM. Therefore, if the exact amount of shrinkage can be registered for each combination of these pieces of data, it will become possible to calculate the dimensions before the shrinkage without performing the measurement to the ADL film.

Figures 8, 9:
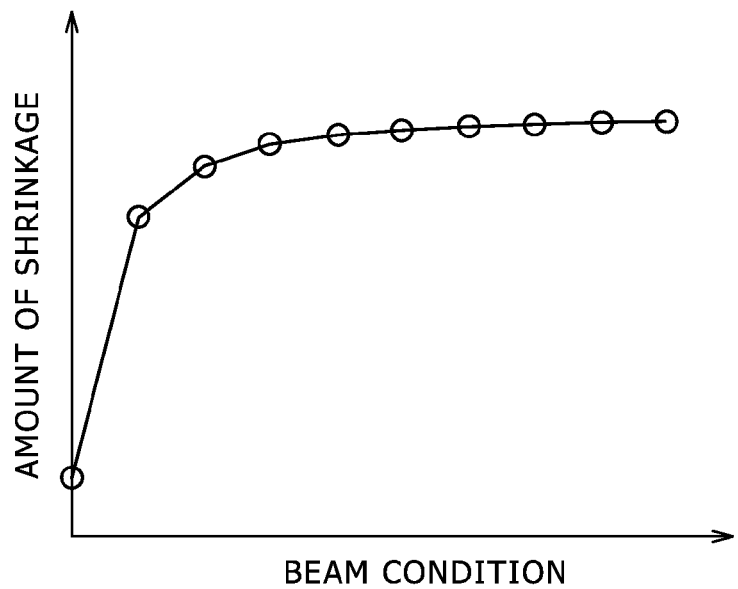
FIG. 8 is a diagram showing a relationship between a beam condition and the amount of shrinkage.
FIG. 9 is a diagram showing one example of the database that stores the beam condition and an offset value of the measurement value or an approximate function being associated with each other.

After performing the measurement of the resist pattern at Step 601, determination as to whether the amount of shrinkage corresponding to a combination of the kind of the above-mentioned pattern and the optical condition is registered (Step 602) is performed. When the amount of shrinkage is registered in advance, the measurement value is corrected based on an arithmetic expression as illustrated by Formula 2 using the amount of shrinkage (Step 603). Here, when the amount of shrinkage is not registered, by performing the measurement as illustrated in FIG. 1, the amount of shrinkage is found (Step 604) and correction of the measurement value is performed (Step 605). This offset value is registered in the memory 404, etc. as a measurement value. In this case, the mount of shrinkage can be used as the offset value when the measurement is done later by storing in relation with a combination of the kind of the pattern and the optical condition. For example, the amount of shrinkage like this is set to be registered in the database as illustrated in FIG. 9 as the offset value of the measurement value. It becomes possible to perform an efficient measurement by referring to such a database at Step 602.

Figure 7:
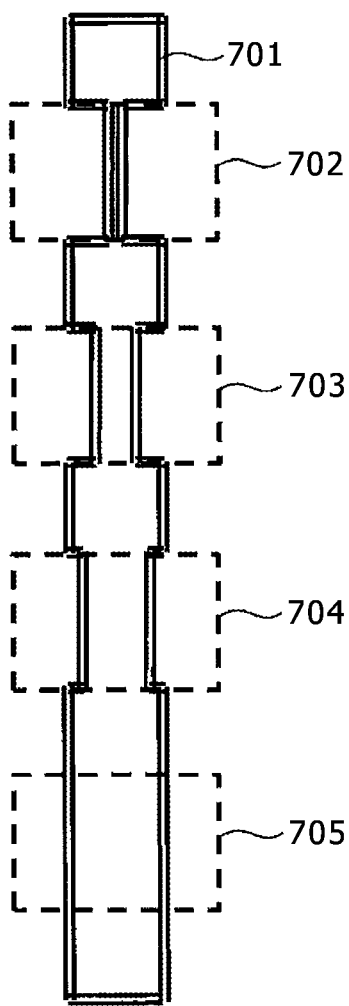
FIG. 7 is a diagram showing one example of a pattern shape when beam scanning is performed at a position at which the resist pattern is different by changing a beam condition.

FIG. 7 is a diagram for explaining an example in which multiple amounts of shrinkage when the beam scanning is performed with the optical condition changed are found in order to build the database as illustrated in FIG. 9. In a pattern 701 illustrated in FIG. 7, the beam scanning to scan regions 702, 703, and 704 at different positions is performed in a stage of the resist, and the line widths F1 to F3 are calculated in respective positions. In this example, the scanning is performed with different conditions (beam current, measurement times, number of frames, landing energy of the beam, scan speed, etc.) for each different scanning position, and thereby the amount of shrinkage is varied. Then, after ALD film formation, the beam is scanned onto the scan regions 702, 703, 704, and 705, and the line widths S1 to S3 (the scan regions 702 to 704) and the line width R (the scan region 705) are measured.

Based on these values, the amount of shrinkage at each position is found as Z1=R−S1, Z2=R−S2, and Z3=R−S3, respectively, and is registered in the database as illustrated in FIG. 9. In the database, each combination of the kind of the pattern and the optical condition is registered, and it is possible to obtain a measurement value whose amount of shrinkage is corrected by referring to the database. Moreover, as illustrated in FIG. 8, by plotting a relationship between the amount of shrinkage and a beam condition and registering the curve as an approximate function, it becomes possible to derive the amount of shrinkage by substitution of the optical condition even under an unknown beam condition.

Figure 10:
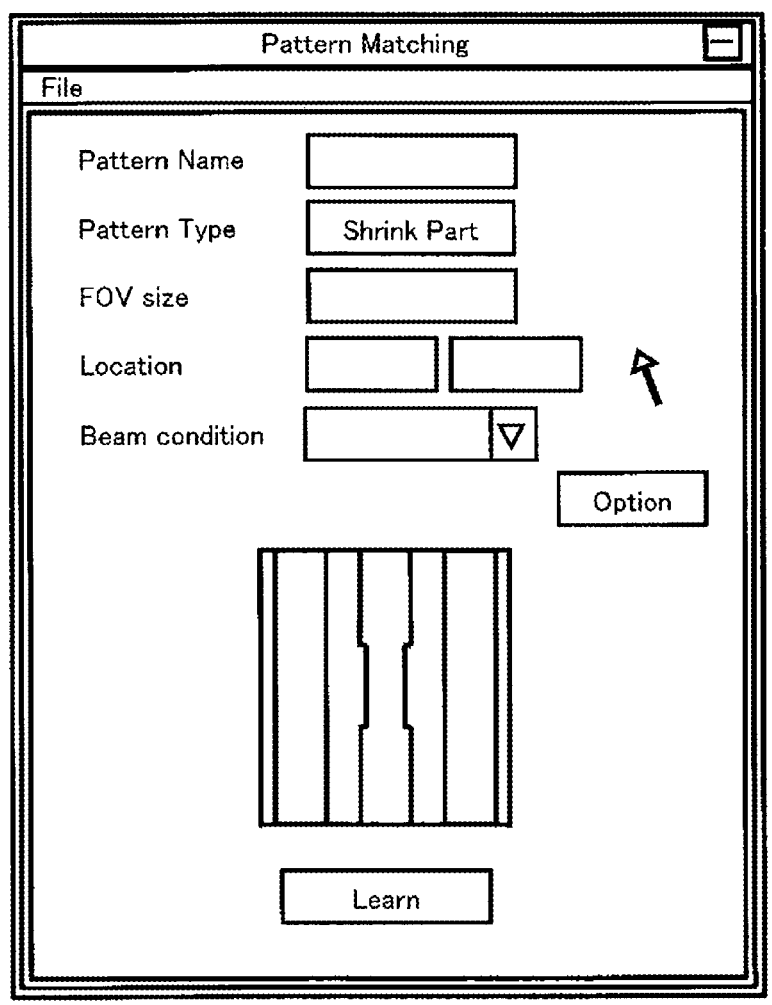
FIG. 10 is a diagram showing one example of a GUI screen for setting a matching condition of template matching.

FIG. 10 is a diagram showing one example of a GUI screen for setting a matching condition when performing the template matching. A technique called the template matching is used for positional alignment in order to set the FOV for measurement in a minute pattern. Although the template matching is a technique of performing alignment by preparing a template that contains patterns having a unique shape and deciding a portion where the degree of coincidence with the template as a matching position is high, the pattern formed by the SADP is a pattern formed with a very narrow pitch less than or equal to the exposure limit that the aligner can reach, and it is often the case that it is a simple repetitive pattern. On the other hand, when a part of the pattern where the simple repetitive patterns continue is deformed by the shrinkage, the portion will have a shape unique to other portions.

Accordingly, in this embodiment, a technique of performing the pattern matching using the unique shape formed by the shrinkage is proposed. The template including a portion that deforms by the shrinkage is created, and matching is executed using the template. Since the measuring point itself serves as the template, it may be good that coordinate information at which the template matching is performed is configured to be registered automatically based on a coordinate specification of the measuring point at the time of setting the recipe.

Moreover, in the case of creating a template based on the design data, it may be good that layout data is created such that a portion corresponding to the scanning region is deformed (shrunk) in a pseudo manner and a template is created based on the deformation layout data. In this case, it may be good that a database for storing a relationship among the optical condition, the amount of shrinkage, and the amount of deformation is prepared, and a proper amount of shrinkage or amount of deformation is read according to an input of the optical condition and is intended to be used for deformation of the layout data. Moreover, in order to make arbitrary deformation possible, a GUI screen in which the layout data in the scanning region of the beam is deformable may be configured to be prepared. The layout data that was subjected to the deformation processing is registered in the recipe as a template after image processing such as smoothing processing is performed thereon.

Figure 11:
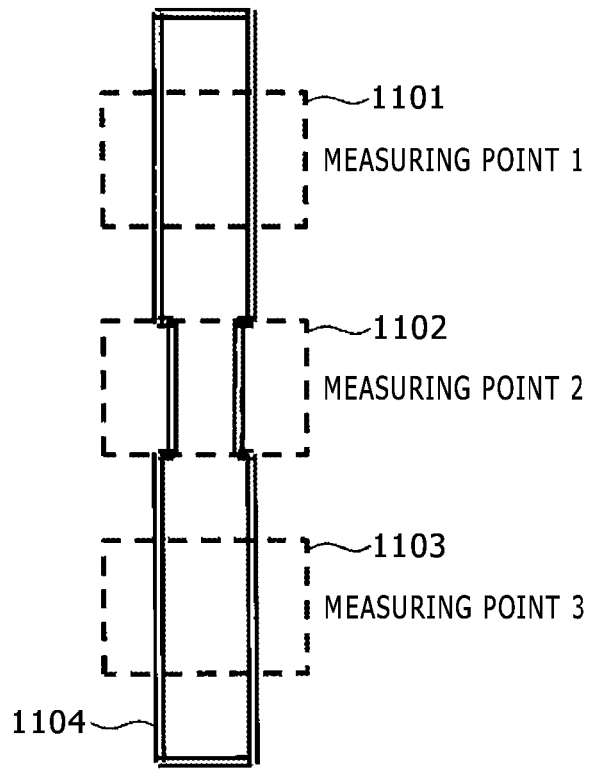
FIG. 11 is a diagram showing an example in which reference regions at two positions and a measurement region (a beam scanning region) in a shrink part are set.
Figure 12:
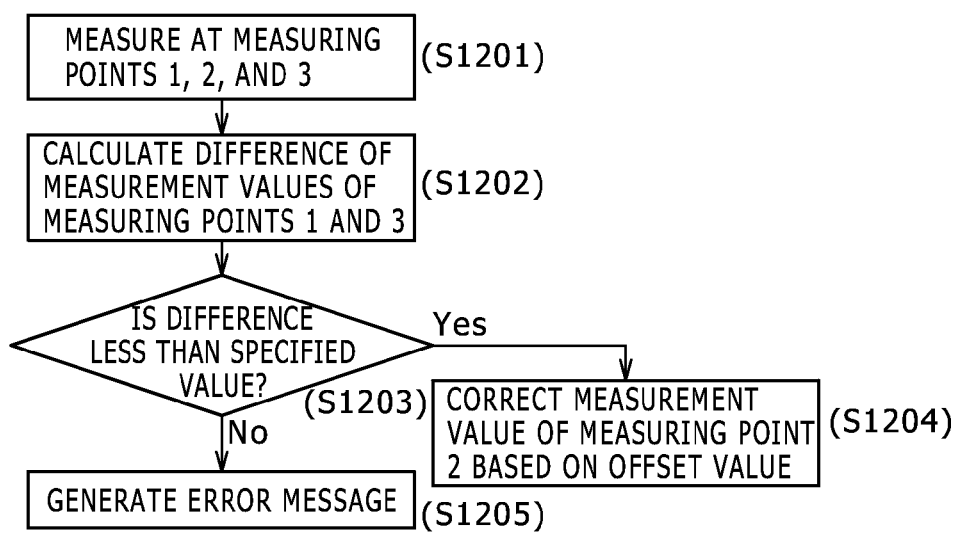
FIG. 12 is a flowchart showing a process of determining a necessity of correction of the amount of shrinkage based on a difference of the measurement values of the reference regions at the two positions.

FIG. 11 is a diagram showing an example in which reference regions 1101, 1103 (measuring points 1, 3) at two or more points are prepared and the line width of a shrink region 1102 (measuring point 2) is measured. For example, in the case where there is a problem in a formation state of the ALD film and its film thickness is not constant, it is conceivable that the measurement method as illustrated in FIG. 1 on a premise that its film pressure is constant can no longer hold. Then, in this example, two reference regions are prepared, a difference of the line widths R1, R2 of the reference regions after the ALD film formation is found (Step 1202), when the difference is zero or less than a specified value, a measurement illustrated in FIG. 1 is performed (Step 1204), and when the difference of the both is more than or equal to the specified value, an error message is generated (Step 1205).

When the difference is judged to be more than or equal to the specified value at Step 1203, it is conceivable that the film pressure is unstable or the shape of the resist is unstable. In such a case, since the premise of the above-mentioned technique of calculating the amount of shrinkage based on the actual measurement value of the ALD film does not hold, it becomes possible to prevent an erroneous measurement from being performed by generating an error message. Moreover, it becomes possible to detect a change of manufacturing conditions.

Figure 13:
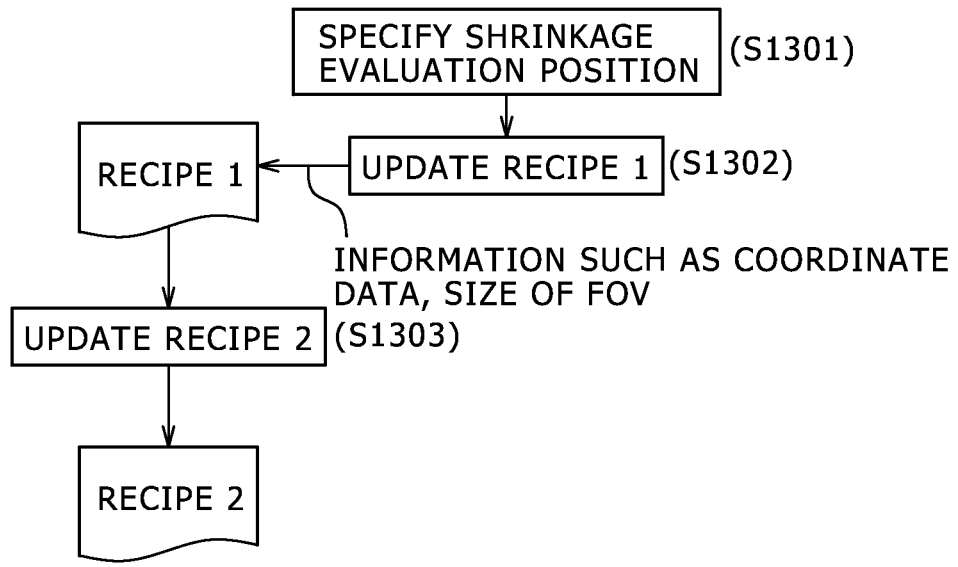
FIG. 13 is a flowchart showing a process of updating two pieces of recipe information based on a specification of a shrinkage evaluation position.
Figure 14:
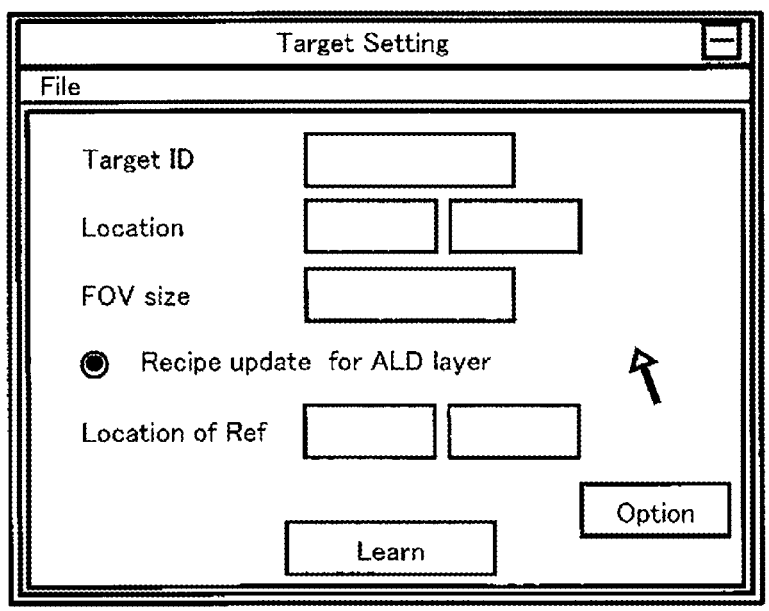
FIG. 14 is a diagram showing one example of the GUI screen for inputting measuring position information for recipe creation.
Figure 15:
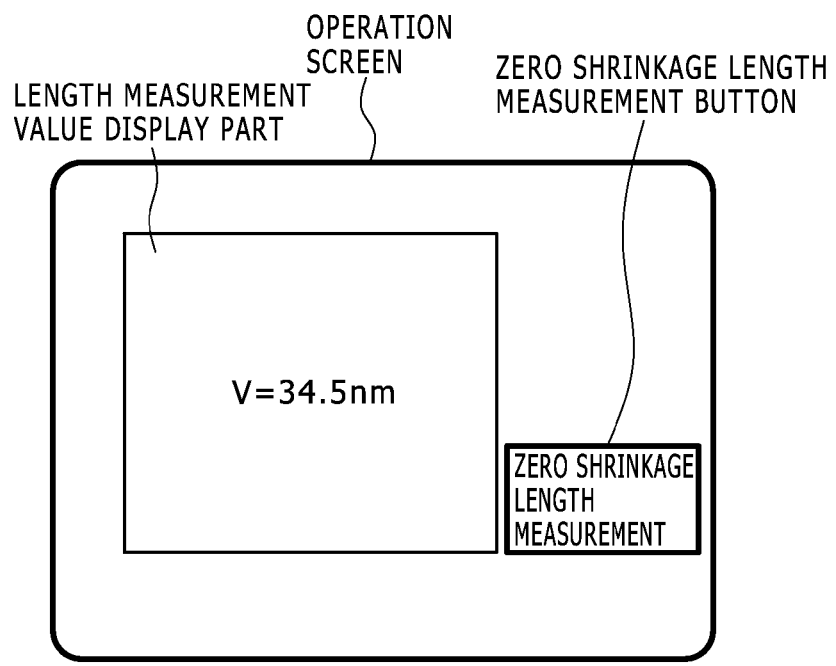
FIG. 15 is a diagram showing one example of an output screen of a length measurement value.

FIG. 13 is a diagram showing a process of updating two kinds of recipes based on a specification of a shrinkage evaluation position. As described above, in the case of this example, the measuring position after resist formation (the measuring position at which the line width F is measured) and the measuring position after the ALD film formation (the measuring position at which the line width S is measured) are the same. Therefore, if the two kinds of recipes can be updated automatically based on specifications of the evaluation position and the dimensions of the FOV, it will become possible to perform recipe creation simply. FIG. 14 is a diagram showing one example of the GUI screen for setting the measuring region of the resist pattern. In addition to the input window for ID to be measured, coordinate data, and a FOV size, it has become possible to perform FOV selection as to whether the FOV size of the recipe 2 (a recipe whose measurement conditions after the ALD film was given are set), coordinate data, etc. are to be updated. Moreover, coordinates in a reference region are also made settable. By providing such automatic updating means, it becomes possible to perform the recipe creation simply.

The SEM illustrated in FIG. 3 is, for example, a length measurement type scanning electron microscope (Critical Dimension-SEM: CD-SEM), in which operation control based on the recipe 1 and the recipe 2 is performed according to an object sample. For example, it is configured so that the recipe 1 and the recipe 2 may be switched based on an input of manufacturing process information by the input device 411 in FIG. 4 or other triggers.

Figure 17:
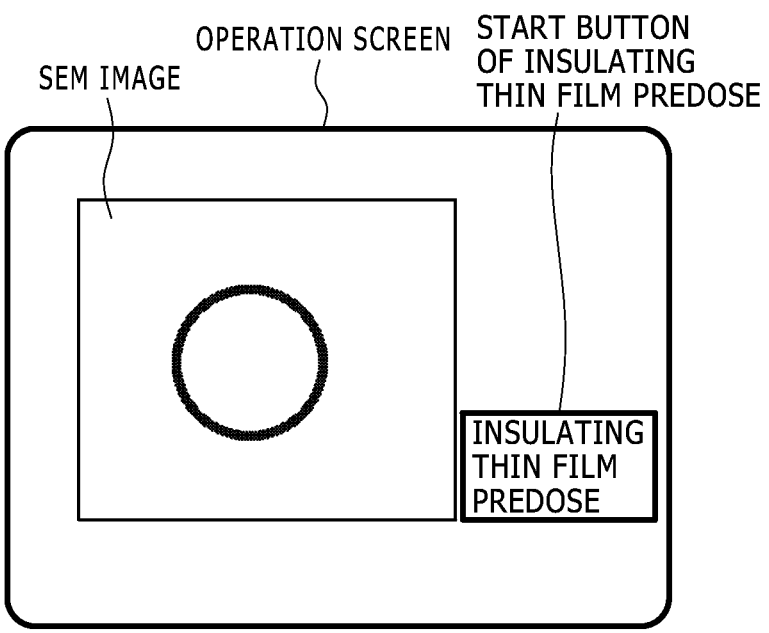
FIG. 17 is a diagram showing one example of a screen for SEM image display in which a predose start button is provided.

FIG. 17 is a diagram showing one example of a display screen displaying the measurement result before the shrinkage (zero shrinkage measurement result). First, the user performs the length measurement of the line width F using the automatic measurement recipe. Then, the ALD film is formed on the wafer surface. Next, this automatic length measurement recipe is made to be read by the length measurement SEM again, and a zero shrinkage length measurement button on an operation screen is pressed. Then, the length measurement SEM carries out the length measurement of the line width S, and in addition to this, carries out automatically the length measurement of the line width R in a place adjoining its upper part and where an electron beam when the line width S is subjected to the length measurement does not hit.

Upon completion of the measurement, V=F+(R−S), a line width that has not shrunk is displayed on the screen.

Figure 16:
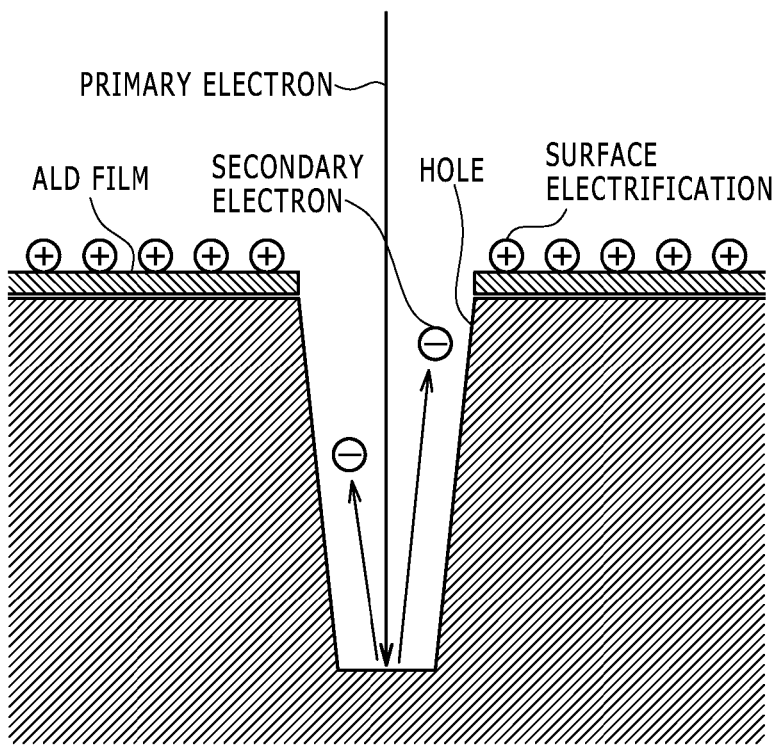
FIG. 16 is a diagram showing one example of a contact hole over which an ALD film is formed.

Next, a suitable measurement method for measuring a pattern of a high aspect ratio will be explained. According to the following technique, there are expected not only estimation of the amount of zero shrinkage but also an effect of improving visual performance to a pattern that is difficult for the SEM to see. FIG. 16 shows an embodiment in the case of measuring a bottom of a deep hole. In a contact hole (HARC) of a high aspect ratio that has a small diameter and is deep, since secondary electrons are hard to come out from the hole bottom to the surface, there is a problem that an SEM image of the hole bottom is difficult to see.

Against this, a technique called predose whereby the electron beam is irradiated in advance before the image is observed and positive charges are charged up on the surface in the vicinity of an entrance of the hole is used. Since the positive charges in the vicinity of this entrance pull up the secondary electrons that come out from the hole bottom and have negative charges, the secondary electrons in the hole bottom become easy to come out to the surface, which gives an effect that the SEM image of the hole bottom becomes easy to observe.

However, since there was an upper limit in an electric charge adsorption density by the predose, it was difficult to observe the hole bottom in a deep HARC pattern, for example, whose aspect ratio was 50 or more.

Then, before carrying out the predose, for example, an ALD thin film of $SiO_2$ is formed to about 4 nm or so on the surface of the pattern. By doing in this way, since $SiO_2$ is a thin film with high insulation, the electric charge adsorption density of the predose can be improved to about four times. If this is done, a power of pulling up the secondary electrons will become stronger, and an observed image of the hole bottom will become clearer.

In order to operate this new measurement method in the length measurement SEM, an insulating thin film predose function is provided in the length measurement SEM. FIG. 17 shows an embodiment of the insulating thin film predose function. In usual predose, since electrified electric charges tend to dissipate easily, predose time is set to, for example, about 20 seconds. On the other hand, when the ALD thin film with high insulation such as SiO is formed on the surface and predose is performed therein, a button of insulating thin film predose that appears on the operation screen of the length measurement SEM is pressed to turn ON. Doing this shortens the predose time to about ½, and it becomes about five seconds in this example. Thereby, since the electric charge adsorption density is twice as high on an insulating thin film, about twice the electric charge adsorption density is obtained as a result, and the observed image of the hole bottom becomes clear. In this occasion, if the electric charge adsorption density is too high, electrostatic attraction caused by absorbed electric charges is too strong, and there is a possibility that a layer in which the hole pattern is formed will be destroyed physically. This is an accident of a generally-called electrostatic discharge. Since, with the use of the insulating thin film predose function of this example, the thin film is configured to be incapable of predose for a long enough time to make the electrostatic discharge occur, the function brings about an effect of preventing the accident of the electrostatic discharge.

Moreover, when the diameter of the entrance of the hole is subjected to the length measurement, the measurement value added with twice a value of the insulating thin film is displayed as the length measurement value. The reason is that the diameter of the hole is measured smaller by an amount of a thickness of the thin film because the thin film is formed from the entrance of the hole to a relatively deep place.

Moreover, contrary to this, there is also an example in which the observed image becomes clearer by forming the ALD thin film of a metallic material having conductivity.

Figure 18:
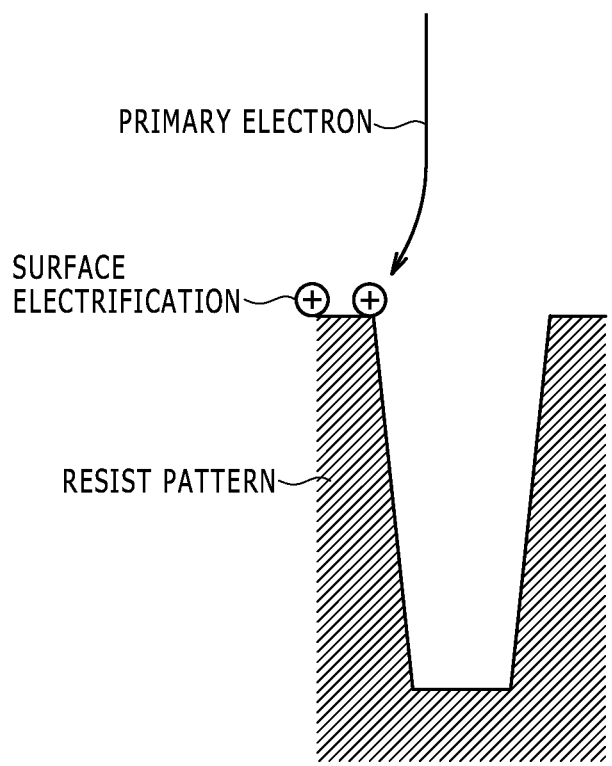
FIG. 18 is a diagram showing a state where a trajectory of an electron beam is deflected under an influence of surface electrification.

FIG. 18 shows an influence of electrification of the resist pattern. This case is a case where the pattern itself is made from a highly insulative material such as $SiO_2$ and photoresist. In such a pattern, hitting of primary electrons for SEM observation generates positive charges on the pattern surface. There may be a case where the SEM image is distorted or is darkened by these bending trajectories of the primary electrons and the secondary electrons.

Figure 19:
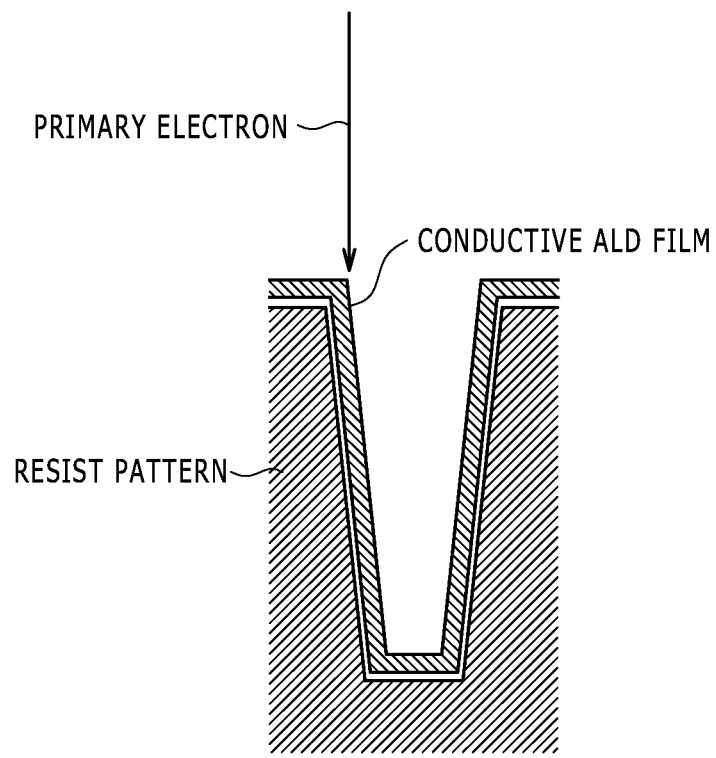
FIG. 19 is a diagram showing an example in which the trajectory deflection of the electron beam is suppressed by forming the ALD film.

Against such a problem, as illustrated in FIG. 19, a conductive ALD film is formed to suppress accumulation of electric charges. The ALD thin film, for example, of Hafnium, is formed to about 2 nm or so on the pattern surface. If doing this, since the pattern surface is covered with a conductive material, the surface is not electrified with electric charges and the problem by the electrification can be reduced.

Also in this case, similarly to the case of the insulating thin film, if the length measurement value of the pattern is a diameter of the hole, a value added with twice the thickness of the thin film from the actual length measurement value is displayed as the length measurement value. Moreover, if the pattern is a line width, its value from which twice the thickness of the thin film is subtracted is displayed as the length measurement value.

LIST OF REFERENCE SIGNS

301 Electron source
302 Extractor electrode
303 Electron beam
304 Condenser lens 305 Scanning deflector
306 Objective lens
307 Sample chamber
308 Sample stage
309, 318 Sample
310 Electron
311 Secondary electron
312 Conversion electrode
313 Detector
314, 316 Gate valve
315 Load-lock chamber
317 Mini-environment
320 Control unit

The invention claimed is:

1. A pattern dimension measurement method for measuring dimensions of a pattern based on a detection signal obtained by scanning a beam onto the pattern formed on a sample, comprising the steps of:
    forming a thin film on the sample containing the pattern after carrying out beam scanning onto a first portion of the pattern;
    acquiring a first measurement value of the pattern on which the thin film is formed by scanning the beam onto a region corresponding to the first portion on which the thin film is formed;
    acquiring a second measurement value of the pattern on which the thin film is formed by scanning the beam onto a second portion that has identical dimensions as those of the first portion on design data; and
    finding an amount of shrinkage of the pattern based on subtraction processing of subtracting the first measurement value from the second measurement value.

2. The pattern dimension measurement method according to claim 1,
    wherein an original dimension before the shrinkage is measured based on addition of the amount of shrinkage and a third measurement value obtained based on the beam scanning onto the first portion before the thin film formation.

3. The pattern dimension measurement method according to claim 1,
    wherein the thin film is an ALD (Atomic Layer Deposition) film.

4. A charged particle beam apparatus comprising:
    a charged particle source for emitting a charged particle beam;
    a scanning position control unit for changing a scanning position of the charge particle beam emitted from the charged particle source; and
    a dimension measurement apparatus for measuring dimensions of a pattern within the scanning positions based on a detection signal obtained by the beam scanning to the scanning position of the charged particle beam,
    wherein the scanning position control unit performs first beam scanning by positioning in advance the scanning position at a first portion on a sample on which the beam was scanned, and subsequently performs second scanning and third scanning by setting the scanning position at the first portion and at a second portion having identical dimensions as those of the pattern located in the first portion on design data, respectively, and
    wherein the dimension measurement apparatus outputs a first measurement value of the first portion and a second measurement value of the second portion based on the detection signal obtained by the second scanning and the third scanning.

5. The charged particle beam apparatus according to claim 4,
    wherein the dimension measurement apparatus finds a third measurement value by subtracting the first measurement value from the second measurement value.

6. The charged particle beam apparatus according to claim 5,
    wherein the dimension measurement apparatus adds the third measurement value and a fourth measurement value obtained based on the first beam scanning.

7. A pattern dimension measurement apparatus for measuring dimensions of a pattern formed on a sample based on a detection signal obtained based on scanning of a charged particle beam, the apparatus comprising:
    a calculation device for, based on a difference of a first measurement value of a first portion that is reduced in pattern dimension by scanning of the charged particle beam and a second measurement value of a second portion having identical dimensions as those of the first portion on design data, calculating an amount of reduction of the first portion.

* * * * *